(12) United States Patent
Dressler et al.

(10) Patent No.: US 10,413,430 B2
(45) Date of Patent: *Sep. 17, 2019

(54) HYDRAULIC DAMPING CYLINDER, IN PARTICULAR FOR A KNEE PROSTHESIS

(71) Applicant: Ossur Iceland ehf, Reykjavik (IS)

(72) Inventors: Janek Dressler, Reykjavik (IS); Thomas Kamm, Reykjavik (IS); Sören Zobirei, Reykjavik (IS); Gabriel Tschupp, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 0 days.

This patent is subject to a terminal disclaimer.

(21) Appl. No.: 15/701,900

(22) Filed: Sep. 12, 2017

(65) Prior Publication Data

US 2017/0367853 A1 Dec. 28, 2017

Related U.S. Application Data

(63) Continuation of application No. 14/970,781, filed on Dec. 16, 2015, now Pat. No. 9,757,253.

(30) Foreign Application Priority Data

Dec. 16, 2014 (DE) .......................... 10 2014 018 712
Jan. 21, 2015 (DE) .......................... 10 2015 100 876

(51) Int. Cl.
*A61F 2/68* (2006.01)
*F16F 9/19* (2006.01)
(Continued)

(52) U.S. Cl.
CPC .................. *A61F 2/68* (2013.01); *A61F 2/64* (2013.01); *F16F 9/062* (2013.01); *F16F 9/19* (2013.01);
(Continued)

(58) Field of Classification Search
CPC ...... A61F 2/68; A61F 2/64; A61F 2002/5006; A61F 2002/5038; F16F 9/062; F16F 9/446; F16F 9/19; F16F 9/34; F16F 9/5126
(Continued)

(56) References Cited

U.S. PATENT DOCUMENTS 2,478,721 A 8/1949 Stewart
5,545,233 A 8/1996 Fitzlaff
(Continued)

FOREIGN PATENT DOCUMENTS

CN 202646218 U 1/2013
DE 202004008014 U1 9/2004
(Continued)

OTHER PUBLICATIONS

Taiwanese Office Action from Taiwanese Application No. 104141675, dated Feb. 13, 2017.

*Primary Examiner* — Pamela Rodriguez
(74) *Attorney, Agent, or Firm* — Workman Nydegger

(57) ABSTRACT

A hydraulic damping cylinder for a prosthetic knee joint, including a housing, a cylinder chamber in the housing and filled with a hydraulic fluid, and a piston arranged in the cylinder chamber and movable by a piston rod. In the housing there are provided at least two separate receiving chambers, which are of different size and are connected to the cylinder chamber by fluid ducts, for hydraulic fluid displaced from the cylinder chamber during a piston movement The receiving chambers are each separated, by a diaphragm, from a compression chamber filled with a compressible fluid that forms an energy store. Upstream of the larger receiving chamber, there is connected a throttle device which forms a flow resistance for the hydraulic fluid flowing into the receiving chamber so that the hydraulic fluid can be (Continued)

distributed to the two receiving chambers in a manner dependent on speed of the piston movement.

18 Claims, 9 Drawing Sheets

(51) Int. Cl.
  *F16F 9/34* (2006.01)
  *F16F 9/512* (2006.01)
  *A61F 2/64* (2006.01)
  *F16F 9/44* (2006.01)
  *F16F 9/06* (2006.01)
  *A61F 2/50* (2006.01)

(52) U.S. Cl.
  CPC ............... *F16F 9/34* (2013.01); *F16F 9/446* (2013.01); *F16F 9/5126* (2013.01); *A61F 2002/5006* (2013.01); *A61F 2002/5038* (2013.01)

(58) Field of Classification Search
  USPC ........... 188/280, 282.3, 284, 285, 288, 289, 188/322.15, 322.19, 322.22; 267/64.11, 267/64.13, 64.15, 64.18, 64.22; 623/26, 623/27, 35–39, 40–46
  See application file for complete search history.

(56) References Cited

U.S. PATENT DOCUMENTS

| | | | |
|---|---|---|---|
| 6,517,585 B1 | 2/2003 | Zahedi et al. | |
| 6,613,097 B1 | 9/2003 | Cooper | |
| 8,231,686 B2 | 7/2012 | Mangiardi | |
| 9,757,253 B2* | 9/2017 | Dressler | ............. A61F 2/68 |
| 2006/0293761 A1 | 12/2006 | Baumann et al. | |
| 2007/0208431 A1 | 9/2007 | Bisinger et al. | |
| 2010/0023133 A1 | 1/2010 | Fairbanks et al. | |
| 2011/0307078 A1 | 12/2011 | Boender et al. | |
| 2013/0013085 A1 | 1/2013 | Smith et al. | |
| 2013/0268091 A1 | 10/2013 | Shen | |
| 2016/0235558 A1 | 8/2016 | Boender et al. | |

FOREIGN PATENT DOCUMENTS

| | | |
|---|---|---|
| DE | 102009056074 A1 | 7/2011 |
| DE | 102008045113 B4 | 8/2011 |
| EP | 1736121 A1 | 12/2006 |
| TW | M415696 U | 11/2011 |
| WO | 2010064063 | 6/2010 |

\* cited by examiner

HYDRAULIC DAMPING CYLINDER, IN PARTICULAR FOR A KNEE PROSTHESIS

CROSS-REFERENCE TO RELATED APPLICATIONS

This application is a continuation of U.S. Ser. No. 14/970,781 filed Dec. 16, 2015, which claims priority to DE 10 2014 018 712.8, filed Dec. 16, 2014 and DE 10 2015 100 876.9, filed Jan. 21, 2015, the priority of these applications is hereby claimed and these applications are incorporated herein by reference.

BACKGROUND OF THE INVENTION

The invention relates to a hydraulic damping cylinder, in particular for a prosthetic knee joint, comprising a housing, a cylinder chamber which is provided in the housing and which is filled with a hydraulic fluid, and a piston which is arranged in said cylinder chamber and which can be moved in the cylinder chamber by way of a piston rod which is introduced into the cylinder chamber.

A hydraulic damping cylinder of said type is used for example in a prosthetic knee joint in order to dampen the flexion movement during which the prosthetic knee joint bends, similarly to the human joint. Said damping is realized in purely fluid mechanical fashion by virtue of the flow of the hydraulic fluid conveyed out of the cylinder chamber into a receiving chamber being correspondingly throttled.

It is also known for a damping cylinder of said type to be equipped with an extension aid. Such an extension aid constitutes an energy store which is charged during the course of the flexion and which, during the course of the extension, that is to say when the prosthetic knee joint is straightened again, is discharged and thereby assists said extension movement. For this purpose, it is known for the damping cylinder to be equipped with a spring element which constitutes the energy store and which is stressed during the course of the flexion and which is relaxed again during the extension. In the case of a damping cylinder of said type, however, the energy storage is purely travel-dependent, that is to say the amount of energy stored in the spring is dependent only on the extent to which the knee joint is bent. That is to say, the stored restoring energy is always the same, regardless of the walking speed of the wearer of the prosthesis, if the prosthetic knee joint is always bent consistently to the same angle during the course of the fast or slow movement. This is however sometimes uncomfortable for the wearer of the prosthesis. This is because, during slow walking, owing to the low step frequency, relatively little extension assistance is sufficient, whereas, during fast walking, owing to the high step frequency, more intense extension assistance would be necessary.

SUMMARY OF THE INVENTION

The invention is thus based on the problem of specifying an improved hydraulic damping cylinder which permits speed-dependent energy storage.

To solve said problem, it is provided according to the invention, in the case of a hydraulic damping cylinder of the type mentioned in the introduction, that, in the housing, there are provided at least two separate receiving chambers, which are of different size and are connected to the cylinder chamber by way of fluid ducts, for hydraulic fluid displaced from the cylinder chamber during a piston movement, which receiving chambers are in each case separated, by way of a diaphragm, with a compression chamber filled from a compressible fluid that forms an energy store, wherein, upstream of the relatively large receiving chamber, there is connected a throttle device which forms a flow resistance for the hydraulic fluid flowing into the receiving chamber, in such a way that the hydraulic fluid can be distributed to the two receiving chambers in a manner dependent on the speed of the piston movement.

The damping cylinder according to the invention is distinguished by two receiving chambers of different size for the hydraulic fluid which is displaced out of the cylinder chamber during a piston movement. Each receiving chamber is assigned a separate compression chamber which is filled with a compressible fluid, normally a gas such as air or nitrogen. The respective receiving chamber and the respective compression chamber are separated from one another by way of a flexible diaphragm. Consequently, if a pressure builds up in the receiving chamber owing to the inflowing, virtually incompressible hydraulic fluid, normally an oil, a deformation of the diaphragm occurs, thus inevitably resulting in a decrease in volume of the compression chamber, which in turn leads to a compression of the fluid, for example air, contained in the compression chamber. Said compressed fluid forms the energy store, and the stored energy is extracted again during the course of the subsequent extension movement, so as to assist the latter.

The two receiving chambers are of different size, and can thus hold different amounts of hydraulic fluid. Depending on which of the receiving chambers a corresponding amount of hydraulic fluid is now supplied to, a different amount of energy is stored in the respective compression fluid. To now be able to vary the distribution of the hydraulic fluid to the two receiving chambers, a throttle device is connected upstream of the relatively large receiving volume, which inevitably requires more hydraulic fluid to flow into it than the relatively small receiving chamber in order to be able to store a similar amount of energy. Said throttle device constitutes a defined flow resistance for the hydraulic fluid flowing into the relatively large receiving chamber.

If a flexion movement now occurs, hydraulic fluid is forced out of the cylinder chamber. During a slow movement, that is to say if the hydraulic fluid flows relatively slowly in the direction of the receiving chambers, the fluid flow is opposed firstly by the flow resistance of the throttle device but secondly also by the resistance formed by the diaphragm of the relatively small receiving chamber. Here, the throttle device is preferably set such that the flow resistance generated thereby is lower than the diaphragm resistance of the diaphragm of the relatively small receiving chamber. Accordingly, the hydraulic fluid flows preferentially into the relatively large receiving chamber, and self-evidently also possibly to a certain extent into the relatively small receiving chamber. The diaphragm assigned to the relatively large receiving chamber is subjected to load, and in the associated compression chamber, energy is stored during the course of the slow flexion movement owing to the amount of fluid flowing in, wherein the amount of energy stored is relatively low owing to the size of the receiving chamber.

If the flow resistance generated by way of the throttle device is set to be slightly higher, the amount of fluid flowing into the relatively small receiving chamber during a slow flexion movement increases, that is to say, overall, more energy is stored. Basically, however, the pressure in both receiving chambers should rise synchronously in the case of very slow movement.

By contrast, in the case of a relatively fast flexion movement, the flow resistance of the throttle device is higher than the diaphragm resistance of the diaphragm assigned to the relatively small receiving chamber. The hydraulic fluid flows preferentially, following the path of least resistance, into the relatively small receiving chamber, and not via the throttle device. This has the effect that, since the volume of the relatively small receiving chamber is not particularly large, intense diaphragm deformation occurs, that is to say the compression fluid in the compression chamber is consequently intensely compressed, giving rise to a high energy input or a large amount of stored energy, which has an additional movement-assisting action during the course of the subsequent extension. The faster the flexion movement, the greater the proportion of hydraulic fluid that flows into the relatively small receiving chamber, because, as described, the flow resistance of the throttle device becomes progressively greater, in relation to the diaphragm resistance, in a speed-dependent manner. Consequently, the faster the flexion movement, the greater the amount of energy that is stored in particular in the energy store assigned to the relatively small receiving chamber, which can be retrieved during the course of the subsequent extension movement for an assistance action.

That is to say, automatic and dynamic gait speed adaptation (auto-adaptivity) of the flexion and extension damping is realized on the basis of fluid mechanics alone. The damping cylinder thus adapts in auto-adaptive fashion to the respective gait speed, and stores different amounts of energy in a speed-dependent manner. In this way, it is possible to ensure optimum setting of the damping from slow walking speed (for example 2 km/h) up to relatively fast walking speed (for example 7 km/h) without the need to dispense with speed-adapted energy return.

To be able to form the different chambers in the housing in a simple manner, it is provided, in a refinement of the invention, that the cylinder chamber is formed at an insert component arranged in the housing. Said insert component, which may self-evidently also be of multi-part form, firstly forms the cylinder chamber. Secondly, it is then possible, between the insert component and the housing itself, for the corresponding receiving chambers and compression chambers to be formed in conjunction with the respective diaphragm.

It is particularly expedient for the flow cross section of the throttle to be adjustable, that is to say for the flow resistance that the hydraulic fluid is subjected to by the throttle device to be variable. In this way, it is then ultimately possible to adjust the level of speed dependency with which the distribution of the hydraulic fluid to the two receiving chambers is to take place. For example, if the flow cross section of the throttle device is set to be relatively large, a relatively high flexion speed is required for the hydraulic fluid to flow predominantly only into the relatively small receiving chamber. By contrast, if the flow cross section is relatively small, and consequently the flow resistance of the throttle device is high, the major part of the hydraulic fluid flows into the relatively small receiving chamber even in the case of a relatively low flexion speed. In this way, it is thus possible to realize gait speed adaptation with regard to the amount of energy stored.

To permit adjustability of the flow cross section, the throttle device may comprise an adjustable throttle element by means of which the cross section of a flow bore leading to the receiving chamber, and thus ultimately a duct cross section, can be varied. The adjustment can consequently be performed by way of a simple screwing-in and screwing-out movement. The throttle element may be guided movably by way of a thread, and can be adjusted by screw motion in order to vary the cross section. Also, the throttle element may be limited in terms of the scope of its movement by way of a setting piece equipped with a thread.

The throttle device is expediently situated in the region of the base of the cylinder chamber, wherein the relatively large receiving chamber is also provided in the region of the cylinder base, so as to surround the latter at least in sections, whereas the relatively small receiving chamber is provided thereabove, in particular in the region of the cylinder cover element. The receiving chambers are consequently arranged one above the other and are connected to the cylinder chamber by way of corresponding fluid ducts.

As described, the two compression chambers provide the energy storage capability. It is basically conceivable for each compression chamber to be filled with the compressible fluid, that is to say for example air or some other gas. Since this is a closed system, the fluid should not escape. To nevertheless provide a refilling facility for technicians, or to apply a certain system pressure in the compression chambers in accordance with the comfort of the wearer of the prosthesis, a reversibly closable fluid supply opening is expediently provided via which compressible fluid can be filled into the compression chambers. Said fluid supply opening is provided on the outer side of the housing, and comprises a corresponding filling port, preferably with an associated 2/2 directional valve. This permits simultaneous filling of both compression chambers, with the filling pressure in both chambers being equal.

It is furthermore advantageous if the two compression chambers are connected to one another by way of a check valve which opens in the presence of a positive pressure in the compression chamber assigned to the relatively large receiving chamber. If, for example during slow walking, only the relatively large receiving chamber is filled because the throttle resistance is lower than the diaphragm resistance of the compression chamber assigned to the relatively small receiving chamber, the pressure in the compression chamber assigned to the relatively large receiving chamber increases with progressive flexion. Since said compression chamber however stores only relatively little energy, because the relatively large receiving chamber has a considerable volume, it is possible by way of the check valve for pressure equalization with respect to the other compression chamber to take place, such that energy is stored in said other compression chamber also.

The respective diaphragm by way of which a receiving chamber is separated from the associated compression chamber is preferably a rubber or plastics diaphragm with adequate flexibility. Said diaphragm is, by way of corresponding fastening sections or fastening means, sealingly fastened at the housing side and, if provided, to the insert component. Since the receiving chambers and compression chambers preferably run around the cylinder chamber, the respective diaphragm is also a ring-shaped component.

It is expedient if, during the course of the flexion, flexion travel dependency of the supply of hydraulic fluid into the receiving chambers is also realized. This is because, in the case of slight flexion, for example flexion of up to 20° or 30°, it is not necessary to store an excessively large amount of energy as extension assistance energy, as the knee joint is scarcely bent. It is only in the case of relatively large bend angles, and thus relatively great flexion travel, that storage of a relatively large amount of energy, in particular by way of the relatively small receiving chamber, is desirable. To permit this, one expedient refinement of the invention provides that, upstream of the receiving chambers, there is connected a switching valve by means of which, in a manner dependent on the position of the piston or of the piston rod, the hydraulic fluid flow can be supplied to the relatively large receiving chamber bypassing the throttle device or via the throttle device. The flexion travel directly influences the piston or piston rod position. By means of the switching valve provided according to the invention, it is now possible in position-dependent fashion for the hydraulic fluid flow to be led into the relatively large receiving chamber either bypassing the throttle device, and consequently, in effect, in unthrottled fashion, or to be led into the relatively large receiving chamber via the throttle device. In the former case, the hydraulic fluid displaced from the cylinder chamber flows substantially into the relatively large receiving chamber, as said inflow is ultimately opposed by virtually no flow resistance aside from the diaphragm resistance of the compression chamber assigned to the relatively large receiving chamber. Said diaphragm resistance is however lower than the diaphragm resistance of the compression chamber assigned to the relatively small receiving chamber. That is to say, the hydraulic fluid flows virtually entirely into the relatively large receiving chamber, and here, only a very small amount of energy is stored in the associated compression chamber. During a further flexion movement, however, the switching valve is actuated and the hydraulic fluid flow passes via the throttle device. Now, the speed-dependent fluid distribution as described above takes effect. In the case of a slow flexion speed, the flow resistance of the throttle device is, as described, lower than the diaphragm resistance of the diaphragm of the compression chamber assigned to the relatively small receiving chamber. Thus, the hydraulic fluid flows preferentially into the relatively large receiving chamber. In the case of a slow movement, the pressure in the two compression chambers rises virtually synchronously, as a result inter alia of the pressure equalization facility by way of the check valve that couples the two compression chambers. However, in the case of a high flexion speed, the flow resistance of the throttle device becomes considerably greater than the diaphragm resistance of the diaphragm assigned to the relatively small receiving chamber, and the hydraulic fluid flows preferentially into the relatively small receiving chamber. With increasing speed, an ever greater amount of kinetic energy is stored in the compression fluid. In the case of a very fast movement, the flow resistance of the throttle device is so high that the hydraulic fluid flows almost exclusively into the relatively small receiving chamber.

Consequently, with realization of the switching valve, both travel dependency and speed dependency are realized.

Here, the switching valve may comprise a stanchion which stands on the cylinder base and which is engaged over by the piston and by the piston rod and which communicates, via a bore, with the cylinder chamber such that hydraulic fluid can be supplied through the stanchion into the relatively large cylinder chamber until the bore is closed the piston that is moved in the direction of the cylinder base or by the piston rod, whereafter the hydraulic fluid flows via the throttle device. The switching valve is thus in the form of a 2/2 directional valve. Depending on the position of the piston or of the piston rod, and thus depending on the flexion angle, the displaced hydraulic fluid can flow into the relatively large receiving chamber either through the stanchion directly, bypassing the throttle device, or via the throttle device. In the case of a relatively small flexion angle, the hydraulic fluid flows virtually without resistance into the relatively large receiving chamber through the stanchion. By contrast, in the case of a relatively large flexion angle, the bore leading into the interior of the stanchion is closed by the piston or the piston rod, such that the hydraulic fluid must inevitably flow via the throttle device in order to pass into the relatively large receiving chamber.

The throttle element expediently engages into the stanchion, wherein the flow bore, the flow cross section of which can be varied by way of the throttle element, is formed in the stanchion. The throttle element, which as described can preferably be varied in terms of its position by way of screw motion and which is guided by way of the thread in the housing, thus extends into the stanchion from below. Said throttle element preferably bears against the inner side of the stanchion. The flow bore is provided on the stanchion, such that the flow bore is opened to a greater or lesser extent in a manner dependent on the position of the throttle element. The hydraulic fluid flowing into the stanchion can flow axially through the throttle element, for which purpose the throttle element has one or more corresponding passage bores, such that a virtually unimpeded inflow into the relatively large receiving chamber is possible.

In a refinement of the invention, it may be provided that, on the piston, there is provided a check valve which opens during a movement in the direction of the cylinder base and by means of which that part of the cylinder chamber which is situated below the piston can be connected to the cylinder chamber which is situated above the piston. By means of said check valve, it is possible for the piston to be hydraulically decoupled from the piston rod. During the course of the flexion movement, the piston rod protrudes progressively further into the cylinder chamber. By means of the check valve, it is now possible for hydraulic fluid to flow from the lower cylinder chamber part into the upper cylinder chamber part. That is to say that, during the course of the flexion movement, the piston does not constitute a displacement element. The amount of hydraulic fluid that is displaced from the cylinder chamber is dependent exclusively on the extent to which the piston rod protrudes into the cylinder chamber, that is to say the piston rod alone constitutes the displacement element.

To form the check valve, provision is expediently made of a sealing ring, which engages around the piston rod, and of a bore, which is provided on the piston and which is engaged over by the sealing ring. The sealing ring lifts from its seat, in which it closes off the bore, on the piston when the piston rod and thus the piston in the cylinder chamber are pushed down. During a movement in the opposite direction, the sealing ring is seated on the piston so as to close off the bore, such that the check valve is closed.

During the extension movement, as described, the piston and the piston rod are moved in the direction of the cylinder cover element again. Here, that cylinder chamber part which is situated above the piston decreases in size. The hydraulic fluid that is forced back out of the receiving chambers flows into the cylinder chamber part situated below the piston. To discharge the oil that must be displaced from the upper cylinder chamber part, which is decreasing in size, provision may be made, in a refinement of the invention, of a throttle valve by means of which that part of the cylinder chamber which is situated below the piston communicates with that part of the cylinder chamber which is situated above the piston, via which throttle valve, during a movement of the piston in the direction of the cylinder cover element, hydraulic fluid flows from the part situated above the piston into the part situated below the piston until, when a defined piston position is reached, said throttle valve is closed. By means of said throttle valve, a damped extension movement is realized, because the speed with which the piston rod can be pulled out of the cylinder chamber is influenced by the fluid flow through said throttle valve. Said fluid flow is possible for example up to a joint bend of 15°; the throttle valve then closes and the two cylinder chamber parts are separated from one another again. A further movement is then scarcely possible if a corresponding means for further hydraulic fluid discharge is not provided. Here, the throttle valve may be designed such that the flow cross section decreases to zero progressively, that is to say not abruptly, such that a certain degree of movement damping is realized within the extension movement.

In a refinement of the invention, the throttle valve may expediently comprise a groove, which runs along the stanchion, and a bore which is formed on the piston or on the piston rod, which bore, when the throttle valve is open, communicates with the groove and with the upper part of the cylinder chamber. Via said bore, it is consequently possible for hydraulic fluid to flow from the upper cylinder chamber part, which is decreasing in size, into the groove provided on the stanchion, and to pass into the lower cylinder chamber part. If said groove then tapers off at its upper end, the above-described damping facility can be realized, because then, as the piston rod is progressively pulled out, the flow cross section of said throttle valve decreases progressively.

If, as described above, it is sought to realize end position damping, that is to say if it is consequently sought for the piston or piston rod to be damped and to be movable into a defined end position without abrupt impacting, the invention provides the arrangement of at least one adjustment throttle valve, by means of which the flow cross section of a hydraulic fluid duct, which connects that part of the cylinder chamber which is situated above the piston to the relatively small receiving chamber, can be varied. Said adjustment throttle valve defines a very small flow cross section of the hydraulic fluid duct, such that a very small amount of hydraulic fluid can pass into the relatively small receiving chamber, from which it flows into the cylinder chamber part situated below the piston. Owing to the small flow cross section, the further extension movement as far as full extension is consequently intensely damped, such that the mechanical components pass into the end position very slowly.

The adjustment throttle valve may for example comprise a throttle screw which is guided by way of a thread so as to be situated in the housing, by means of which throttle screw the cross section of the hydraulic fluid duct can be varied. It is preferable for two adjustment throttle valves to be provided, wherein the adjustment throttle valve is secured, in particular sealed, in a fixed position so as to define a minimum throughflow. A technician can, by way of the first adjustment throttle valve, adjust the end position damping, that is to say can consequently vary the flow cross section of the hydraulic fluid duct by screw-motion adjustment of the throttle screw, in accordance with the comfort of the wearer of the prosthesis. To prevent the flow cross section from inadvertently being fully closed, resulting in no further movement, that is to say resulting in the cylinder being, in effect, blocked, the second adjustment throttle valve is provided, which defines a minimum throughflow and which is fixed in a secured position and cannot be actuated by the technician or user.

As described, in the damping cylinder, an exchange of the hydraulic fluid takes place between the cylinder chamber and the receiving chambers. During a flexion movement, hydraulic fluid is forced into the receiving chambers, and during an extension movement, the hydraulic fluid flows back out of the receiving chambers. This circuit preferably comprises a hydraulic fluid reservoir, though this is not imperative. To form a hydraulic fluid reservoir of said type, it is preferable for an additional receiving chamber to be provided for hydraulic fluid that flows back out of the relatively large receiving chamber during a movement of the piston in the direction of the cylinder cover element. Said additional receiving chamber is preferably realized in the interior of the piston rod which is connected via a check valve to the interior of the stanchion, which check valve, during a movement, opens owing to the hydraulic fluid pressure imparted by the hydraulic fluid flowing from the relatively large receiving chamber into the stanchion. The piston rod-side receiving chamber consequently fills during the course of the extension movement, whereas said receiving chamber is evacuated during a flexion movement.

To permit said evacuation in a simple manner, it is expediently provided that, on the stanchion, there is provided at least one aperture which is arranged in the region of or above the check valve and at which a groove, which is formed on the outer side of the stanchion and which extends in the direction of the cylinder base, opens out. During the course of the flexion, when the piston rod protrudes into the cylinder chamber and consequently runs over the stanchion, a decrease in volume of the receiving chamber in the piston rod interior inevitably occurs. The hydraulic fluid cannot flow through the blocked check valve. Instead, said hydraulic fluid flows, through the one or more apertures provided in the stanchion, and bypassing the check valve, into corresponding grooves formed on the outer side of the stanchion, from which grooves said hydraulic fluid can flow into the lower cylinder chamber part regardless of the position of the piston rod relative to the check valve or stanchion. It is preferable for two mutually oppositely situated apertures and corresponding mutually oppositely situated grooves to be provided.

Aside from the damping cylinder itself, the invention also relates to a prosthetic knee joint comprising a damping cylinder of the above-described type.

The various features of novelty which characterize the invention are pointed out with particularity in the claims annexed to and forming a part of the disclosure. For a better understanding of the invention, its operating advantages, specific objects attained by its use, reference should be had to the drawings and descriptive matter in which there are illustrated and described preferred embodiments of the invention.

DETAILED DESCRIPTION OF THE INVENTION

Figure 1:
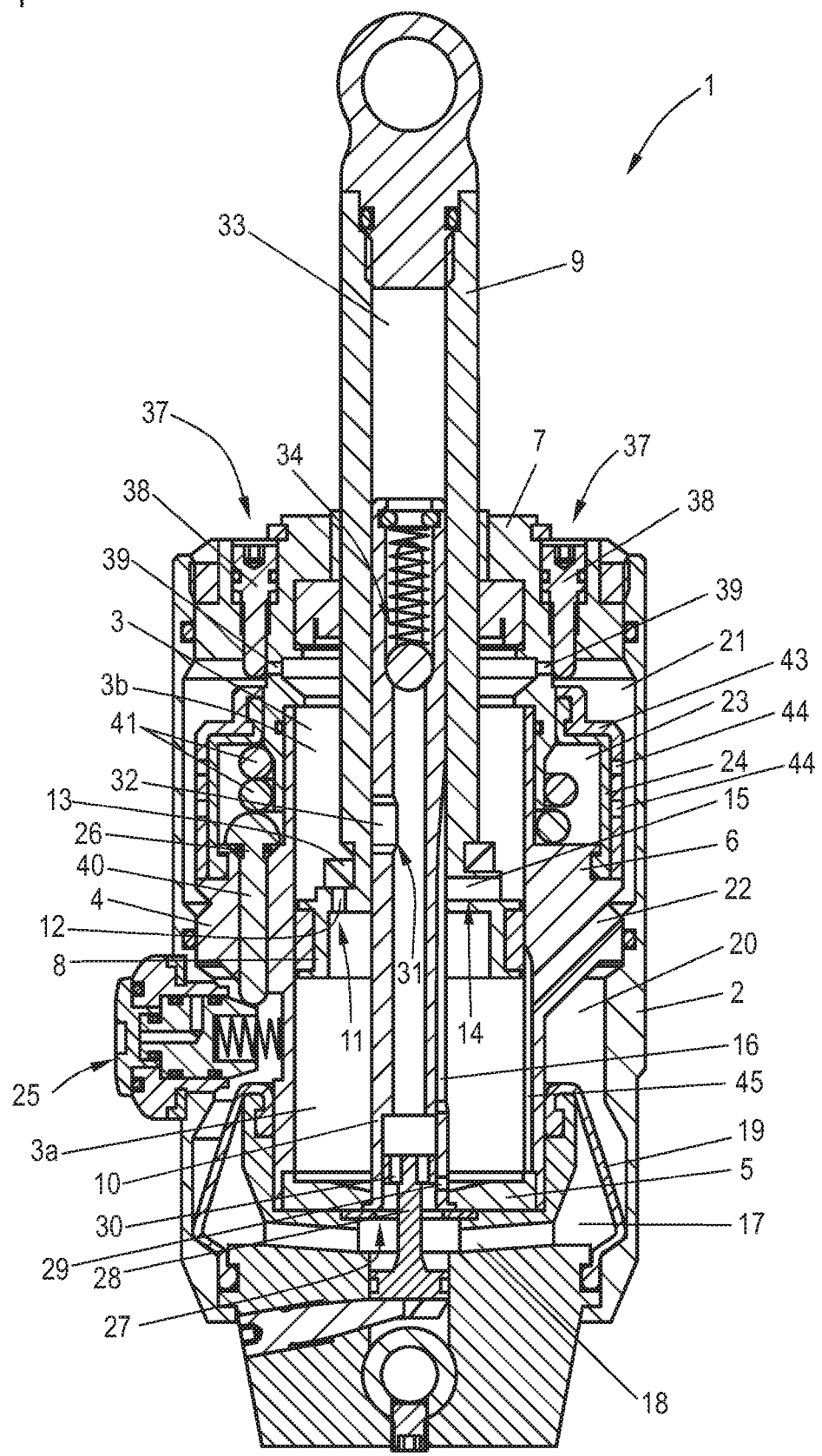
FIG. 1 shows a sectional view through a hydraulic damping cylinder according to the invention.

FIG. 1 shows a hydraulic damping cylinder 1 according to the invention which is suitable for a prosthetic knee joint. Said hydraulic damping cylinder comprises a housing 2, in the interior of which there is arranged an insert component 4 which has a cylinder chamber 3. The insert component 4 is of multipart form and comprises a cylinder base 5 and a component body 6 which radially closes off the cylinder chamber 3. At the top side, the cylinder chamber 3 is closed by way of a cylinder cover element 7 which is fixed to the housing.

In the interior of the cylinder chamber 3 there is provided a piston 8 which is connected to a piston rod. The piston 8 and the piston rod 9 run or engage around a stanchion 10 which is fastened to the cylinder base 5. The piston 10 divides the cylinder chamber 3 into a lower cylinder chamber part 3a and an upper cylinder chamber part 3b. On the piston and on the piston rod there is provided a check valve 11, which is realized by way of a bore 12 in the piston and a sealing ring 13 arranged on the piston rod. The check valve 11 opens when the piston is moved in the direction of the cylinder base 5. Said check valve closes in the event of a movement in the opposite direction. Furthermore, a throttle valve 14 is provided which comprises a bore 15, provided in the piston rod, and a groove 16 which is provided along the outer side of the stanchion and which tapers in an upward direction, see FIG. 1.

Between the housing 2 and insert component 4 there are formed various receiving and compression chambers. A first, relatively large receiving chamber 17 is provided, which is provided in the region of the cylinder base 5 and which extends in ring-shaped fashion around the insert component 4. One or more fluid ducts 18, which communicate(s) with the cylinder chamber 3, open(s) into said first, relatively large receiving chamber. The relatively large receiving chamber 17 is separated from a first compression chamber 20 by way of a diaphragm 19. In the compression chamber 20 there is accommodated a compressible fluid, for example air or some other gas. As a result of the hydraulic fluid situated in the cylinder chamber 3 flowing into the receiving chamber 17, the flexible diaphragm 19, which is a rubber or plastics diaphragm, is deformed, and the volume of the compression chamber 20 is reduced. This is associated with a compression of the compression fluid, and thus storage of energy.

Also provided is a relatively small receiving chamber 21 which is provided in the region of the upper cylinder end. The receiving chamber 21 is connected from the cylinder chamber 3 by way of one or more hydraulic ducts 22. Said receiving chamber is assigned a second compression chamber 23, which is separated from the receiving chamber 21 likewise by way of a flexible diaphragm 24. The diaphragm 24 is engaged over by a sleeve 43 which is perforated with holes 44 via which the hydraulic fluid acts on the diaphragm 24. Also, in said compression chamber 23, there is situated a compression fluid, for example likewise air or a gas. The receiving chamber 21 is smaller than the receiving chamber 17. It is also possible for the diaphragm 24 to be slightly stiffer than the diaphragm 19, and to consequently have a higher diaphragm resistance. If hydraulic fluid is conveyed from the cylinder chamber 3 into the receiving chamber 21, it is the case there, too, that the pressure causes a deformation of the diaphragm 24, and thus a reduction of the compression chamber volume and consequently a compression of the fluid situated there. In this way, too, storage of energy in the compression fluid is realized.

The compression chambers 20 and 23 can be filled with the compression fluid via a fluid supply opening 25. The fluid supply 25 is in the form of a filling port with a 2/2 directional valve. Also provided is a check valve 26 which permits pressure equalization in the presence of a positive pressure in the compression chamber 20 in relation to the compression chamber 23. Also, the compression chambers 20 and 23, and also the receiving chambers 21 and 17, run in ring-shaped fashion around the insert component 4, and the diaphragms 19 and 24 are correspondingly also ring-shaped components.

Also provided is a throttle device 27 comprising a throttle element 28 which is guided in adjustable fashion on the housing 2 or on the stanchion 10 by way of a threaded connection. Said throttle element engages into the stanchion 10 as shown in FIG. 1. The throttle device 27 furthermore comprises a flow bore 29 which is formed on the stanchion 10 and the flow cross section of which can be correspondingly varied by way of corresponding positioning of the throttle element 28. By means of the throttle device 27, it is consequently possible for the free flow cross section to the relatively large receiving chamber 17 to be adjusted, and consequently for a variable flow resistance to be set for hydraulic fluid passing out of the cylinder chamber 3 to the receiving chamber 17.

The throttle element 28 has multiple longitudinal bores 30 which enable hydraulic fluid flowing into the interior of the flow pipe 10 to flow into the receiving chamber 17 while bypassing the throttle itself, that is to say in this case the flow bore 29 of reduced flow cross section.

In order that hydraulic fluid can pass into the interior of the flow pipe 10, or a switchable fluid flow either via the throttle device 27 or the flow bore 29 or bypassing the latter is possible, a switching valve 31 is provided, comprising the stanchion 10, or a bore 32 formed in the stanchion 10, which bore is exposed when the piston 8 is raised; that is to say, then, the piston 8 or the piston rod 9 is situated above the bore 32. In this case, from the point at which a certain piston or piston rod position is reached, the piston rod 9 closes off the bore 32. For as long as said bore is still open, hydraulic fluid can pass from the cylinder chamber 3 into the stanchion 10, and a fluid flow into the receiving chamber 17 via the longitudinal bores 30, bypassing the throttle 27 itself, is possible. With the closure of the bore 32, the switching valve 31 is closed. During a continued lowering movement, the hydraulic fluid can then flow into the receiving chamber 17 only via the throttle device 27 or the flow bore 29 with corresponding flow resistance.

Figure 9:
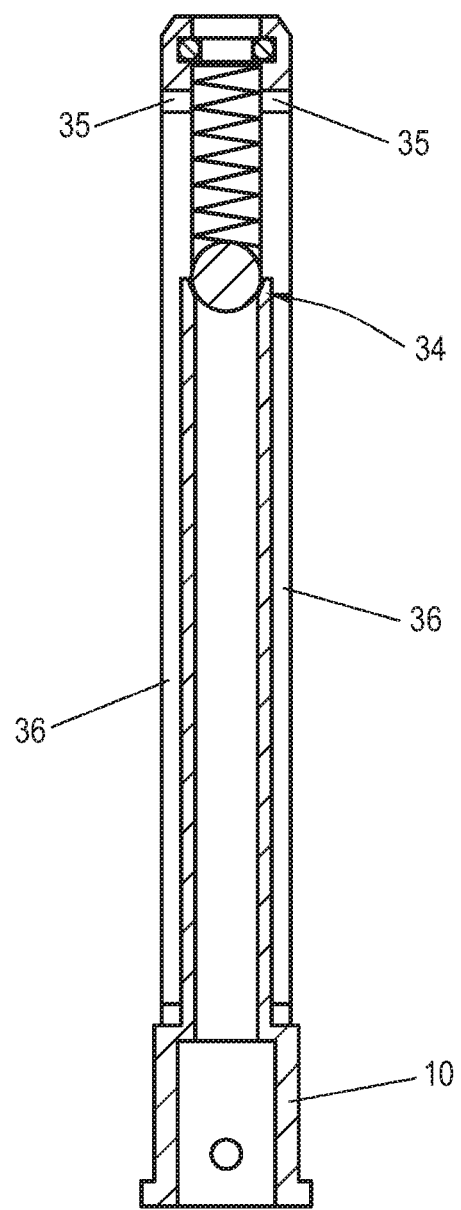
FIG. 9 shows a side view of the stanchion of the damping cylinder for illustrating the apertures and external grooves.

Also provided is an additional receiving chamber 33 for hydraulic fluid. Said receiving chamber 33 is realized in the interior of the piston rod 9. Hydraulic fluid can pass into said receiving chamber 33 via a check valve 34 integrated in the stanchion 10. Said check valve 34 is opened when the piston rod 9 is pulled out of the cylinder chamber 3. In this case, as will be discussed below, hydraulic fluid flows out of the receiving chamber 17 into the stanchion 10 and opens the check valve 34. During an opposite movement, the hydraulic fluid can flow out of the receiving chamber 33 into the lower cylinder chamber part 3a, because on the stanchion 10—see FIG. 9—there are provided two mutually opposite apertures 35 which are arranged in the region of the check valve 34.

Provided opposite one another on the outer side of the stanchion 10 are two longitudinally running grooves 36 which open out at the apertures 35. Consequently, if the piston rod 9 is pushed downward, the receiving chamber 33 decreases in size. The hydraulic fluid situated therein then flows via the apertures 35 and the grooves 36 into the lower cylinder chamber part 3a.

Finally, two adjustment throttle valves 37 are provided which are realized on the cylinder cover element 7 by way of corresponding threaded screws 38. By means of these, the flow cross section of an associated fluid duct 39, which connects the upper cylinder chamber part 3b to the relatively small receiving chamber 21, is adjusted. In this way, end position damping is realized, which will be discussed in more detail below. One of the two adjustment throttle valves 37 can be adjusted by the technician. For this purpose, it is merely necessary for the threaded screw to be correspondingly screwed in or screwed out. The other adjustment throttle valve 37 is adjusted and secured in position at the factory, such that a minimum throughflow is always realized in order to prevent a situation in which the joint cannot pass into the fully extended position.

Figure 2:
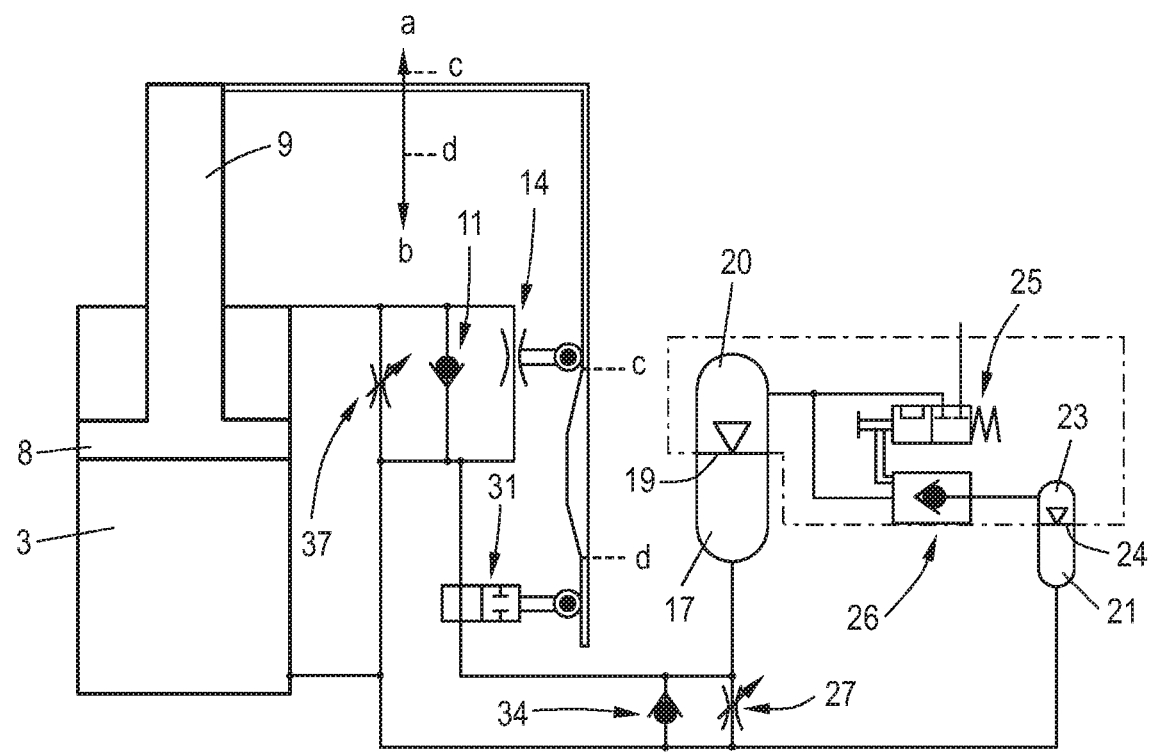
FIG. 2 shows a hydraulic and pneumatic block circuit diagram.

FIG. 2 shows a corresponding block circuit diagram of the damping cylinder 1 from FIG. 1. The figure shows the main hydraulic and pneumatic elements. Illustrated at the cylinder side is the cylinder chamber 3, the piston 8 and the piston rod 9. Also shown are the two receiving chambers 17 and 21, with their associated compression chambers 20 and 23 belonging to the pneumatic system, separated by way of the respective diaphragms 19 and 24. The illustration also shows the throttle device 27 which is arranged in the inflow to the relatively large receiving chamber 17, whereas a throttle of said type or similar is not provided in the inflow to the relatively small receiving chamber 21.

Also shown by way of example is an adjustment throttle valve 37, and also the piston-side check valve 11 and the throttle valve 14, by means of which valves the upper and lower cylinder chamber parts 3a, 3b can communicate with one another in a manner dependent on the direction of movement of the piston 8 or of the piston rod 9.

Also illustrated is the important switching valve 31 by means of which bypassing of the throttle device 27 is possible in a manner dependent on the piston/piston rod position.

Also shown, as illustrated by the dash-dotted line, is the pneumatics part comprising the already described compression chambers 20 and 23 and also the fluid supply opening 25, that is to say the already described filling port with the 2/2 directional valve. Finally also shown is the check valve 26, formed from the plunger 40 shown in FIG. 1, which in the example shown is spring-loaded against two elastic rings 41, which form the opening resistance.

A distinction is made between a hydraulics side and a pneumatics side. The hydraulics side comprises all of the volumes filled with hydraulic oil. These are the cylinder chamber 3, all of the hydraulic fluid ducts, the receiving chambers 17 and 21, the interior of the stanchion 10 and also the interior of the piston rod 9, that is to say the additional receiving chamber 33. As hydraulic fluid, use is commonly made of an oil.

The pneumatics side comprises the two compression chambers 20 and 23 and the region of the fluid supply opening, if the latter is not already regarded as part of the compression chamber 20. Said pneumatic regions are filled with a compressible fluid, as already described, normally air or some other gas.

Figure 3:
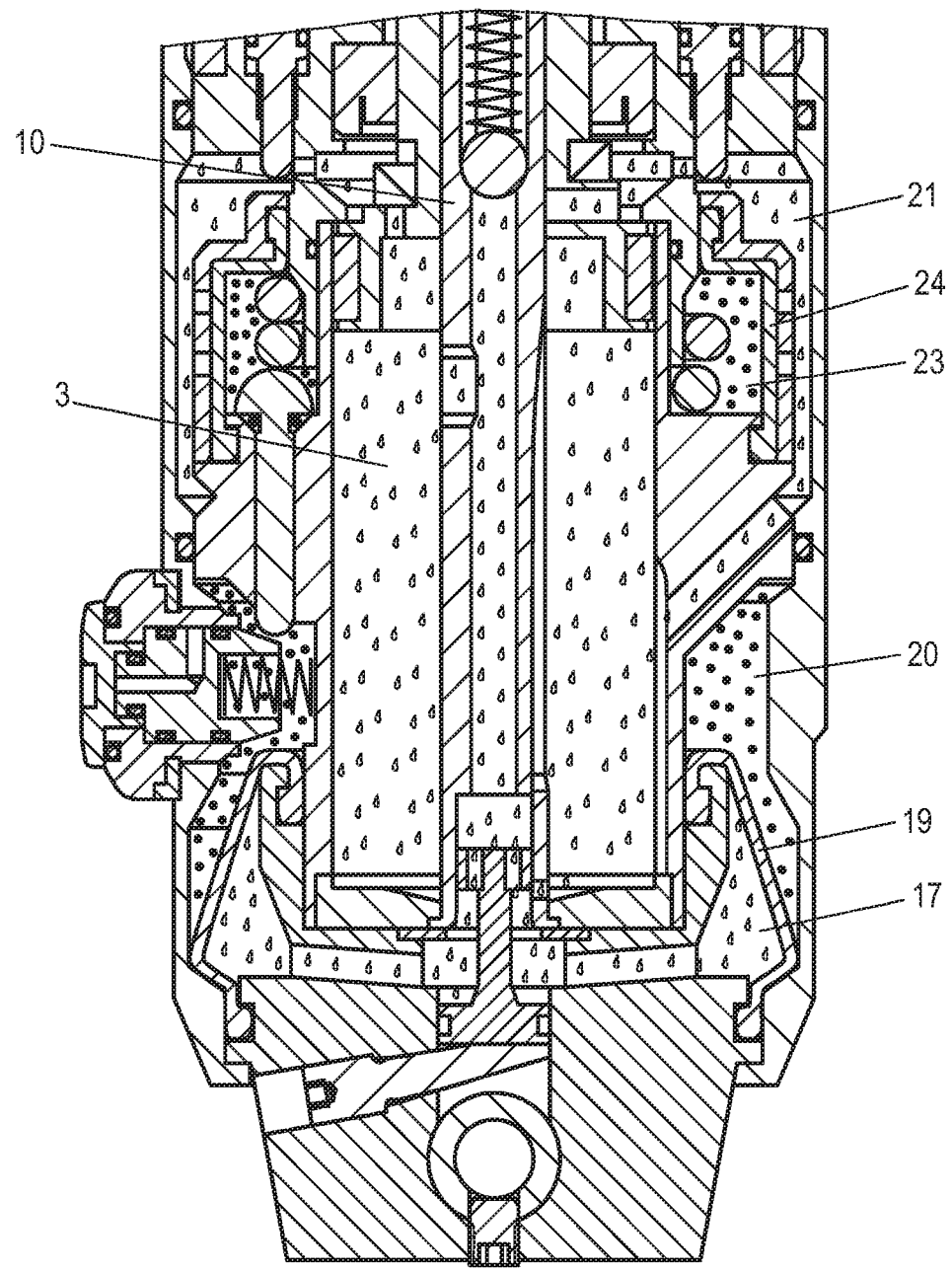
FIG. 3 shows a partial view of the damping cylinder from FIG. 1 for illustrating the receiving and compression chambers.

By way of example, in FIG. 3, in a partial view of the damping cylinder 1 from FIG. 1, the regions filled with the hydraulic fluid are correspondingly denoted by a droplet symbol, whereas the regions filled with the compression fluid are correspondingly indicated by dots. Although not shown here in any more detail, hydraulic fluid is self-evidently also present in the interior of the piston rod 9 (not shown in its entirety).

The functional principle of the damping cylinder 1 will now be described on the basis of FIGS. 4-8. The compression chambers 20 and 23 have been filled with the compression fluid via the fluid supply device 25. The same pressure prevails in both, because equalization is possible by way of the check valve 26. The direction of movement of the piston is indicated by way of respective arrows, which point downward or upward. The hydraulic fluid flow is illustrated by dashed arrowed lines, wherein a relatively thick arrowed line denotes a greater fluid flow than a relatively thin arrowed line.

Figure 4:
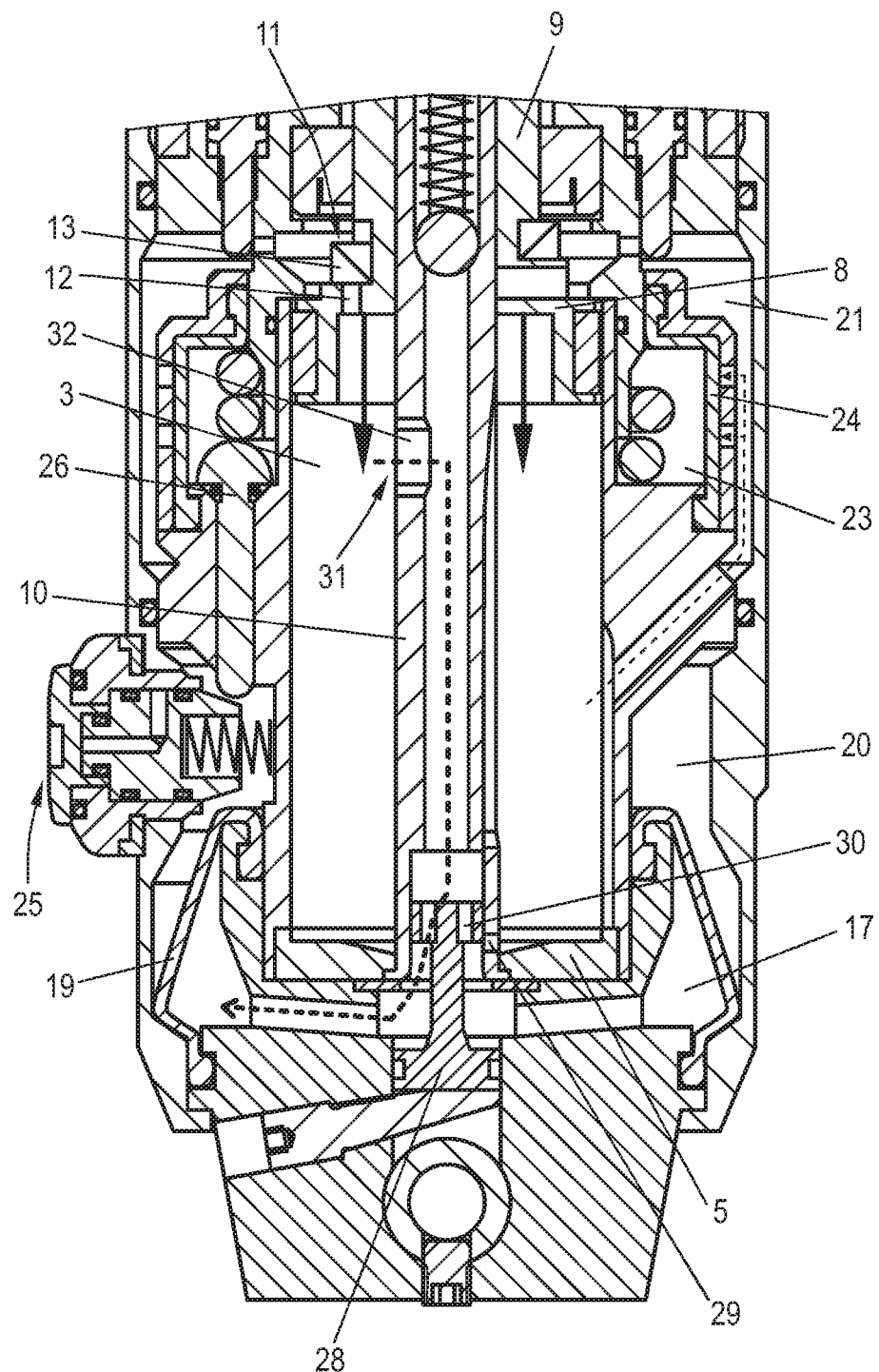
FIG. 4 shows a view corresponding to FIG. 3 at the start of the flexion movement, with switching valve open.

FIG. 4 shows a partial view of the damping cylinder, in the case of which the piston 8 and the piston rod 9 are in a pulled-out position situated at the end stop. The prosthetic knee joint into which the damping cylinder 1 is installed is consequently extended. The wearer of the prosthesis now begins to bend the prosthetic knee joint, that is to say initiate the flexion. This has the effect that the piston rod 9 is pushed into the cylinder chamber 3. At the same time, the piston 8 is self-evidently also moved downward in the direction of the cylinder base 5. Said movement is shown by the two thick arrows in FIG. 4. During said movement, the check valve 11 opens, that is to say the sealing ring 13 is lifted out of its sealing seat against the piston 8 and the bore 12 is open. The piston 8 is consequently hydraulically decoupled from the piston rod 9. This has the effect that the only displacing element protruding into the cylinder chamber 3 is the piston rod 9. The protruding-in of the piston rod 9 causes the hydraulic fluid to be displaced. The displaced hydraulic fluid flows into the corresponding receiving chambers 17 and 21, as will be described in more detail below.

At the start of the flexion movement, the switching valve 31 is open, that is to say the bore 32 is not closed off by the piston rod 9. This makes it possible, as illustrated by the relatively thick dashed arrowed line, for hydraulic fluid to flow into the interior of the stanchion 10. Said hydraulic fluid flows through the longitudinal bores 30 in the throttle element 28 and thus passes into the receiving chamber 17 while bypassing the throttle 27 itself, that is to say the flow bore 29 of set flow cross section. A flow bypassing the throttle 27 is thus realized, and the hydraulic fluid is not subjected to any significant flow resistance.

The predominant part of the hydraulic fluid flows into the relatively large receiving chamber 17. A relatively small part flows into the relatively small receiving chamber 21, as illustrated by the dashed, relatively thin flow arrows. This is because the diaphragm resistance to which the hydraulic fluid is subjected by the flexible diaphragm 24 is considerably greater than the diaphragm resistance imparted by the diaphragm 19. A flow resistance across the throttle device 27 is not realized in this case, as said throttle device is ultimately bypassed. For this reason, since the main fluid flow passes into the relatively large receiving chamber 17, the corresponding flow arrows to the latter are also considerably thicker than the flow arrows leading into the relatively small receiving chamber 21.

The flow bypassing the throttle device 27 is possible only as far as a certain degree of flexion, for example as far as up to 30°. Up to a 30° bend, it is consequently the case that the hydraulic fluid is not subjected to any significant flow resistance as it flows into the large receiving chamber 17, and thus the hydraulic fluid flow is independent of the speed with which the flexion is performed.

Figure 5:
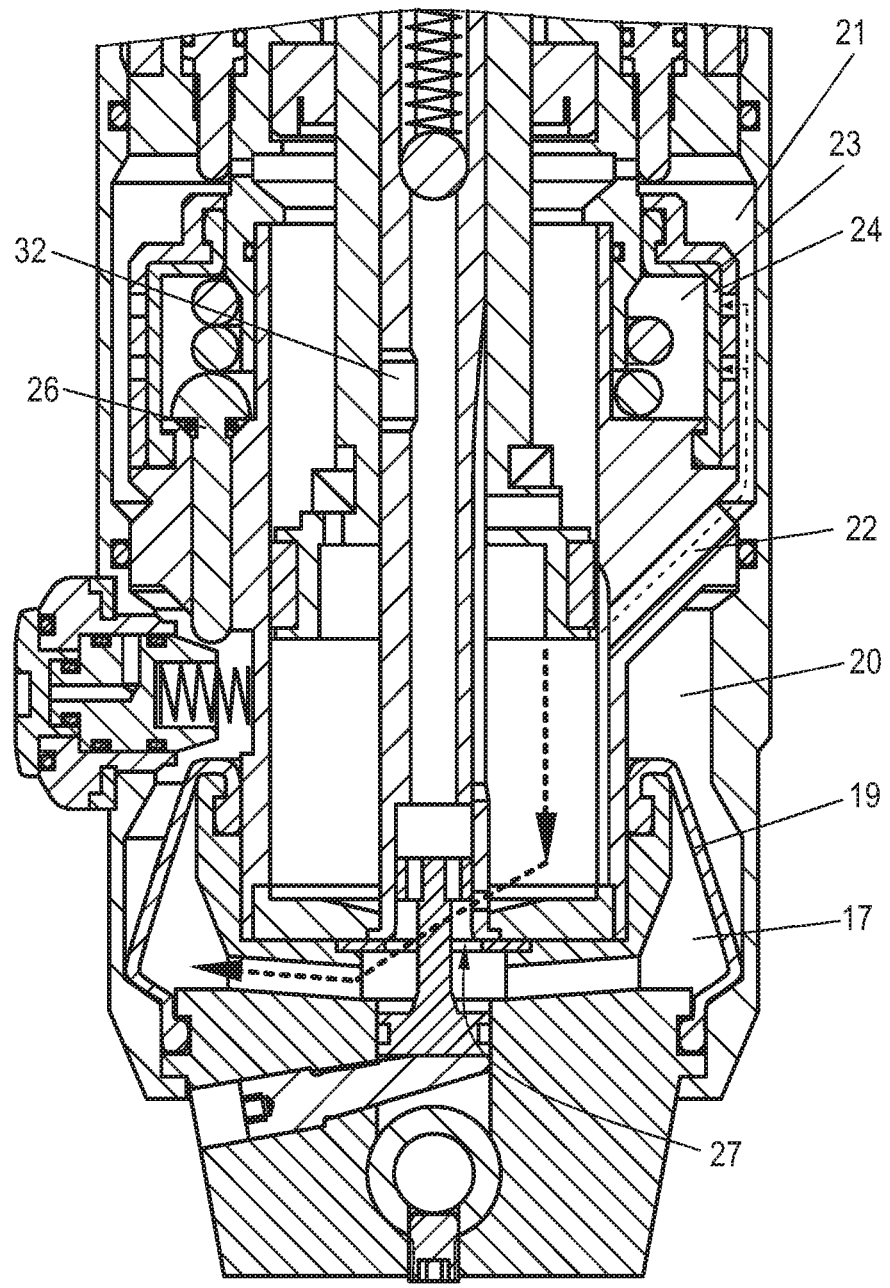
FIG. 5 shows a view corresponding to FIG. 4 during the continued, slow flexion movement, with switching valve closed.

However, beyond a flexion of 30°, which is taken as an example in the description, the switching valve 31 is closed, that is to say the bore 32 is closed, because the piston rod 9 is moved deeper still into the cylinder chamber 3, in this regard see FIG. 5. A further hydraulic fluid flow into the interior of the stanchion is not possible, and the hydraulic fluid must imperatively flow via the throttle device 27, that is to say via the flow bore 29, in order to pass into the relatively large receiving chamber 17. Proceeding from this point in time, that is to say immediately upon the closure of the bore 32, the speed-dependent adaptation takes effect. This is because, from this point onward, the distribution of the hydraulic fluid that is forced out of the cylinder chamber 3 is dependent on the speed of the flexion movement.

FIG. 5 shows the situation in which the flexion movement takes place slowly. Proceeding from the described 30° flexion, the hydraulic fluid can flow only counter to the relatively high diaphragm resistance of the diaphragm 24 assigned to the relatively small receiving chamber 21, or counter to the flow resistance of the throttle device 27. In the case of a relatively low flexion speed, the flow resistance of the throttle device 27 is lower than the diaphragm resistance of the diaphragm 24 of the relatively small receiving chamber. Thus, the hydraulic fluid flows preferentially into the relatively large receiving chamber 17. In this way, the pressure therein rises, a deformation of the diaphragm 19 occurs, and thus a slight increase in pressure in the lower compression chamber 20 occurs. Only a small fraction flows into the relatively small receiving chamber 21, as illustrated by the dashed, arrowed flow lines, which are again of different thickness. In the event that the pressure in the compression chamber 20 becomes higher than the pressure in the compression chamber 23, pressure equalization can be performed by way of the check valve 26.

The further the throttle device 27 is closed, that is to say the further the flow resistance of the throttle device 27 is consequently increased, the more hydraulic fluid flows into the relatively small receiving chamber 21, as the ratio of throttle or flow resistance and diaphragm resistance changes. However, the more hydraulic fluid flows into the relatively small receiving chamber 21, the more energy is stored in the compression fluid in the compression chamber 23, which energy can subsequently be recovered for the extension movement. In the case of very slow flexion movement, however, the pressure in both receiving chambers 17 and 21 increases virtually synchronously, such that—also in conjunction owing to the pressure equalization facility by way of the check valve 26—a similar pressure prevails in the compression chambers 20 and 23.

Figure 6:
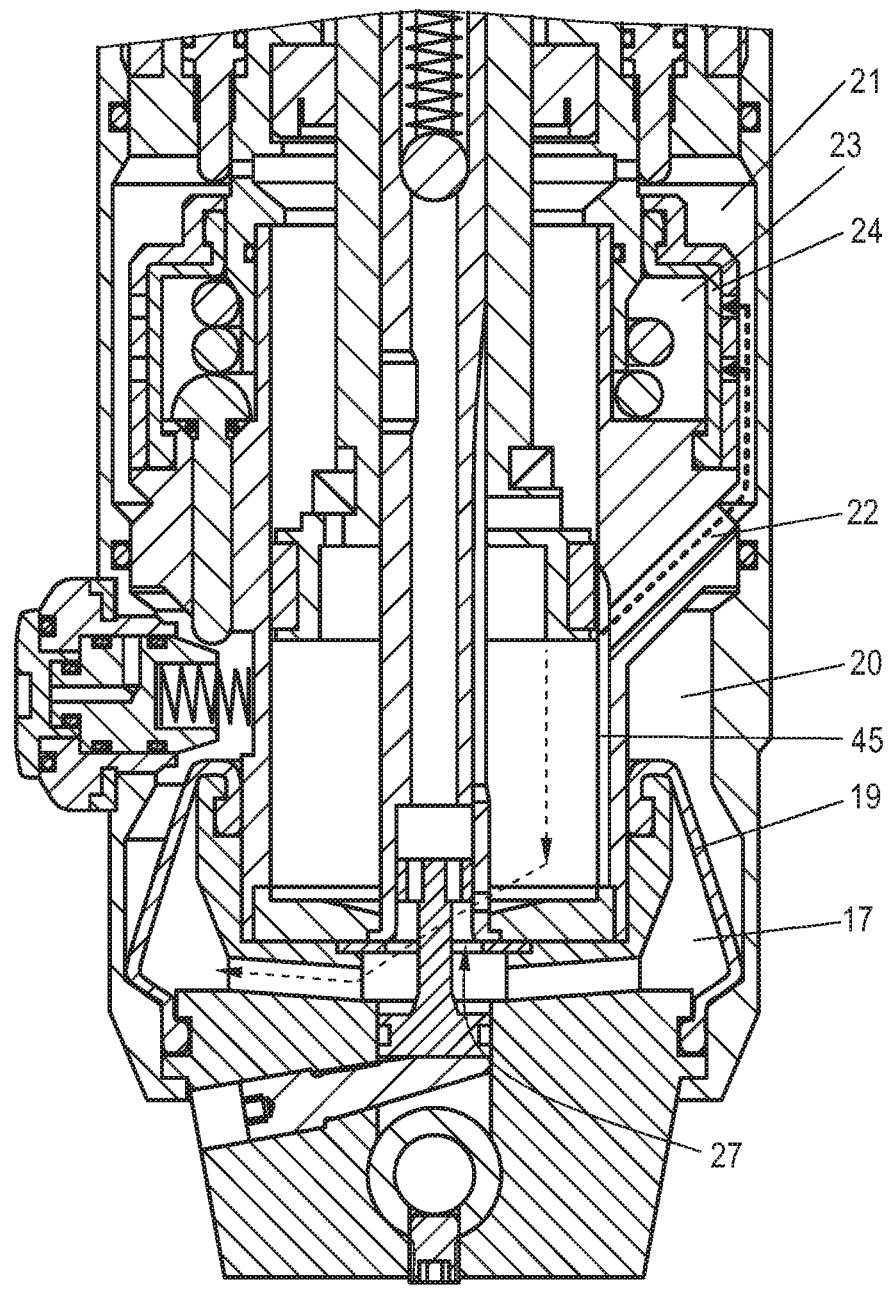
FIG. 6 shows a view corresponding to FIG. 5 during a fast flexion movement, with switching valve closed.

By contrast, FIG. 6 shows the situation when the flexion takes place quickly, or very quickly, with switching valve 31 closed. In the case of a high flexion speed and thus a high speed with which the piston rod 9—which as before is the only displacing element owing to the hydraulic decoupling of the piston 8 from the piston rod 9—protrudes in, the flow resistance of the throttle device 27 becomes considerably greater than the diaphragm resistance of the diaphragm 24 of the relatively small receiving chamber 21. Thus, in a speed-dependent manner and with increasing speed, the hydraulic fluid fraction that flows into the relatively small receiving chamber 21 becomes progressively greater compared with the small fraction that continues to flow via the throttle device 27 into the relatively large receiving chamber 17. An intense deformation of the diaphragm 24, and thus an intense compression of the compression fluid in the compression chamber 23, occur. This results in a high input of energy, that is to say a large amount of energy is stored in the compression fluid. A pressure equalization between the compression chambers 20 and 23 is not possible in this case because the check valve is closed in said direction. In the case of a very fast flexion movement, the flow resistance of the throttle device 27 is so high that the hydraulic fluid flows virtually exclusively into the relatively small receiving chamber 21. An inflow into the relatively small receiving chamber 21 is possible at all times even when the piston 8 has moved downward further beyond the fluid duct 22, as the hydraulic fluid always passes to the fluid duct 22 via a groove 45 which is provided on the inner side of the insert part 4 and which opens out at the fluid duct 22.

Thus, as is evident, the flexion speed determines the distribution of the hydraulic fluid to the two receiving chambers 17 and 21, and thus the amount of energy that can ultimately be stored for the subsequent extension movement. The higher the flexion speed, the greater the amount of energy that is stored in the compression fluid, in particular in the compression chamber 23, and vice versa.

The displacement of the hydraulic fluid out of the cylinder chamber 3 takes place until the flexion, that is to say the bending of the joint, comes to an end. This is then followed by the extension, that is to say the straightening of the joint. Said situation is shown, at the start of the extension movement, in FIG. 7.

Figure 7:
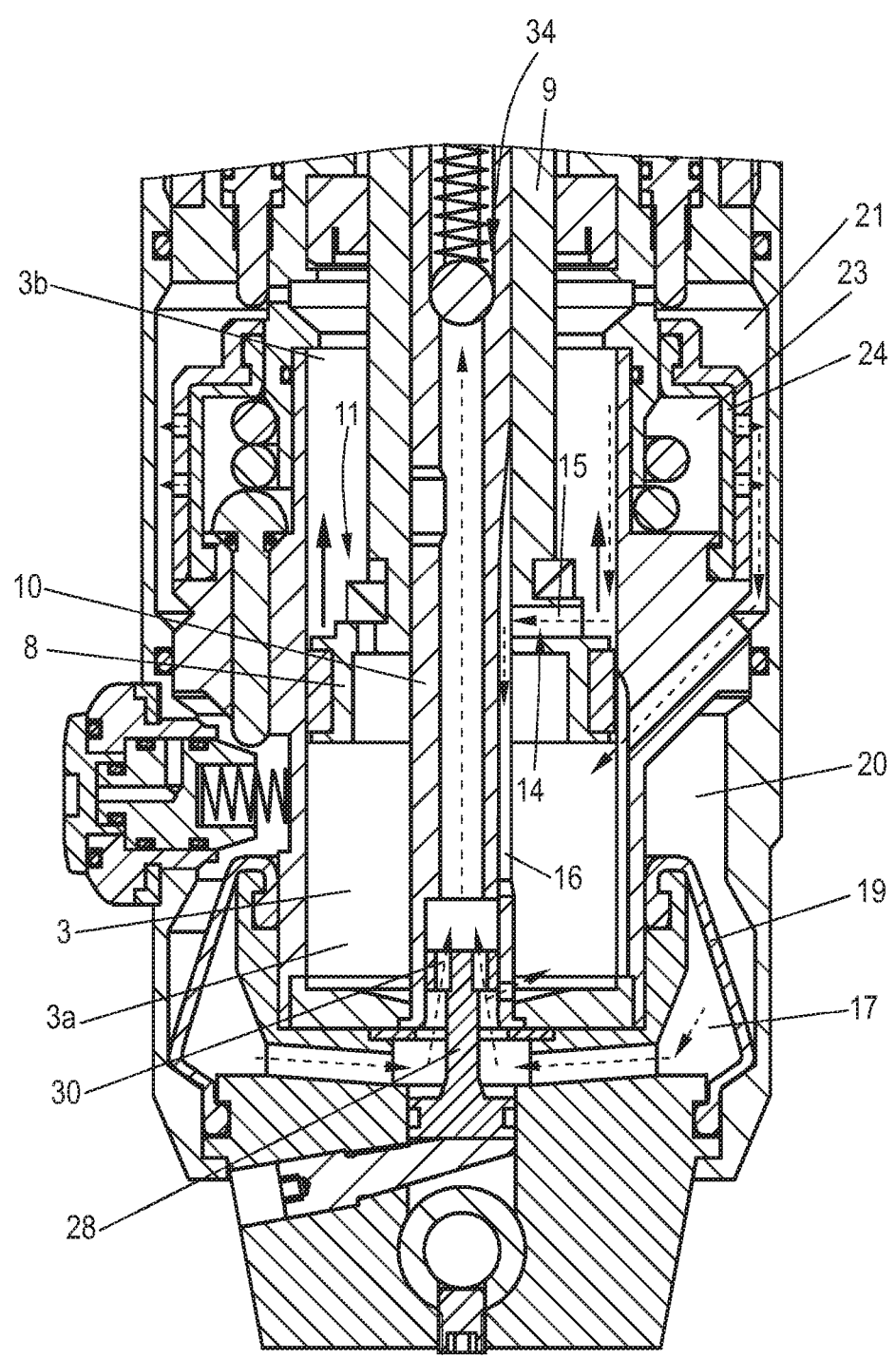
FIG. 7 shows a view proceeding from FIG. 6 at the start of the extension movement.

During the extension movement, the piston rod 9 together with piston 8 is pulled out of the cylinder chamber 3 again, and these move upward as seen in FIG. 7, as illustrated by the two movement arrows.

The situation shown in FIG. 7 arises at the start of an extension movement following a preceding slow flexion during which the pressures in both compression chambers 20 and 23 have increased uniformly and are consequently equal. In this case, the previously displaced hydraulic fluid flows from the two receiving chambers 17 and 21 back into the cylinder chamber 3, or in this case into the lower cylinder chamber part 3a. This is illustrated by the correspondingly dashed arrowed flow lines. Said return flow is driven in each case by the compressed compression fluids in the compression chambers 20 and in particular 23. If, during slow flexion, the pressures in the two compression chambers 20 and 23 are approximately equal, only a low level of extension assistance is provided.

If a fast flexion took place previously, a pressure difference exists between the two compression chambers, which pressure difference may, depending on the flexion movement, amount to several bar to several 10 bar. The more hydraulic fluid has flowed into the relatively small receiving chamber 21, the greater the amount of energy stored in the compression chamber 23, which energy can now be recovered. The flexible diaphragm 24 presses with high pressure against the hydraulic fluid and pushes the latter with corresponding intensity out of the relatively small receiving chamber 21 into the cylinder chamber 3. The greater said return flow, or the higher the pressure of said return flow, the more intense is the assistance force during the course of the extension movement, that is to say the greater is the angular acceleration at the start of the extension movement. The fluid flowing back out of the relatively small receiving chamber at high pressure into the cylinder chamber part 3a however also flows, owing to the pressure difference that exists, via the throttle device 27 into the large receiving chamber, and thus the latter is filled further, in association with a slight pressure increase in the associated compression chamber 20. That is to say, in this case—by contrast to the situation shown in FIG. 7—the lower flow arrows point toward the relatively large receiving chamber 17. This takes place until an equalization of pressures has occurred. Thereafter, with continued extension movement, the hydraulic fluid flows from both receiving chambers into the cylinder chamber part 3a, as shown in FIG. 7. The extension assistance that is then generated is dependent on the remaining residual energy still stored in the two compression chambers 20 and 23.

The throttle valve 14 is open as before, as the bore 15 is still situated adjacent to the groove 16, see FIG. 7. That is to say hydraulic fluid can flow from the upper cylinder chamber 3b, which is decreasing in size owing to the pulling-out movement of the piston and of the piston rod, into the lower cylinder chamber 3a via the throttle valve 14. As before, the piston 8 and the piston rod 9 are hydraulically decoupled from one another, whereby in turn, the piston rod surface is the only displacement element. At the same time, because the hydraulic fluid flows from the relatively large receiving chamber 17 into the interior of the stanchion 10 through the throttle element 28 or the longitudinal bores 30 therein, as shown in FIG. 7, and because the switching valve 31 is closed as before, the pressure in the interior of the stanchion increases. The check valve 34 now opens under the action of pressure, such that the hydraulic fluid can also flow into the additional receiving chamber 33 in the piston rod 9. The check valve 11 is closed during the entire extension movement.

Figure 8:
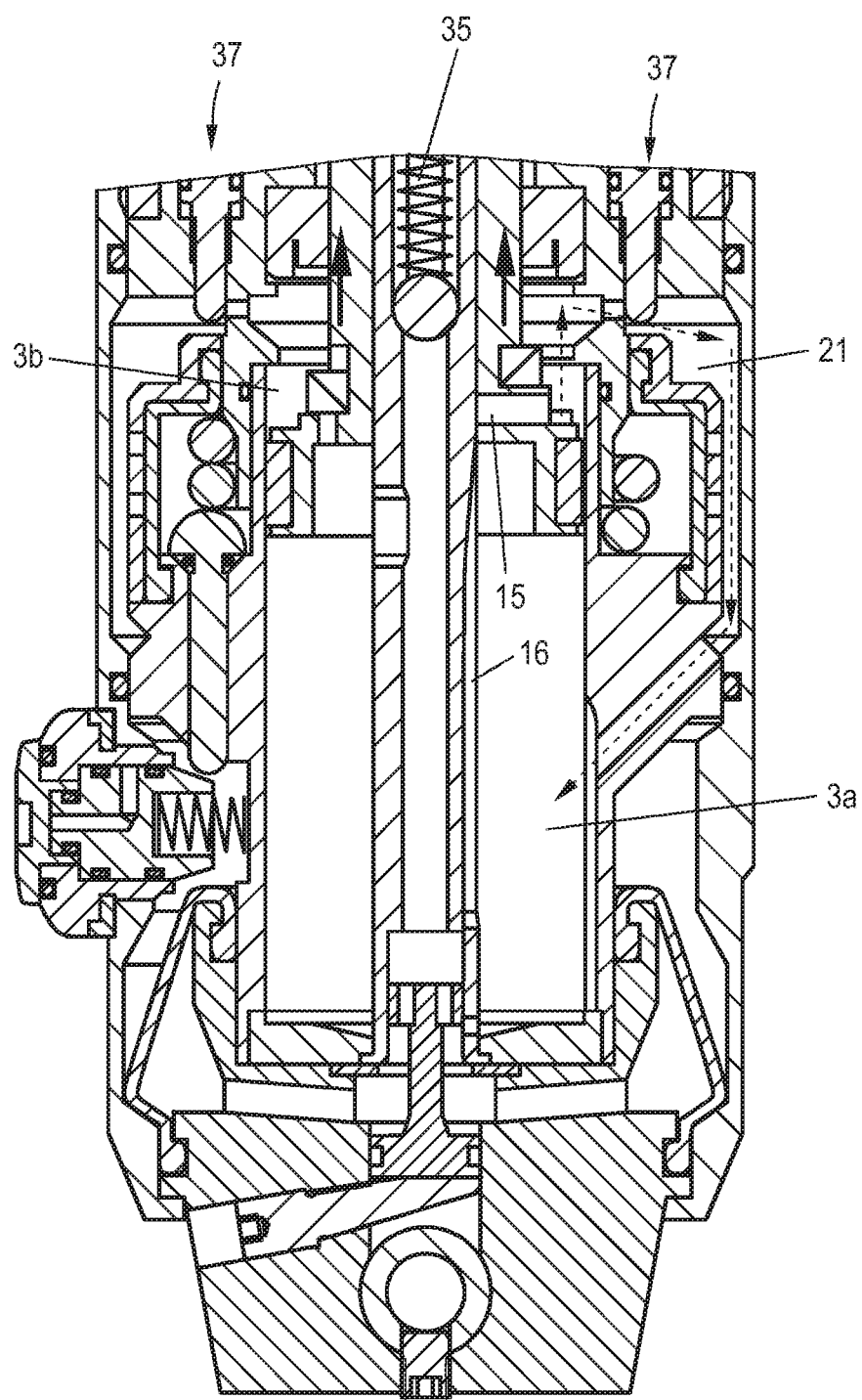
FIG. 8 shows a view during the continued extension movement and abutment against the end stop.

Depending on the amount of energy stored, a fast extension movement or intense movement assistance is consequently possible by way of the recovered energy. This is the case until the throttle valve 14 is open. As described, the groove 16 however continuously tapers off slowly, that is to say decreases to zero, in the region of its upper end. Now, when the piston rod 9 has been pulled out to a sufficient extent, the flow cross section of the bore 15 slowly also closes, such that when a particular position is reached, for example at a degree of bending of 15°, the throttle valve 14 is closed. During a further movement, as illustrated in FIG. 8 by the two movement arrows, it is now necessary for the hydraulic fluid to flow out of the cylinder chamber 3b, which continues to decrease in size, or out of the residual volume that still remains above the piston 8, via the two adjustment throttle valves 37 into the relatively small receiving chamber 21, and via the latter into the lower cylinder chamber part 3a. Since the throttle valve 14 and the check valve 11 are now closed, the piston 8 and piston rod 9 are now hydraulically coupled, that is to say the hydraulic effective surface area now also includes the piston surface area.

If, by way of the tapering-off groove 16, the extension movement was already damped toward the end thereof because the free flow cross section of the bore 15 slowly closes, end position damping is realized by way of the adjustment throttle valves 37. This is because the adjustment throttle valves 37 permit only an extremely small throughflow, such that only a small, intensely damped movement of the piston 8 into its end position is possible. As described, one of the adjustment throttle valves 37 is fixed in position and ensures a minimum throughflow, whereas the other can be adjusted in order to set the end position damping.

When the end position is reached, the extension movement is complete. This is followed by another flexion movement, proceeding from the situation as per FIG. 4 and the movement of the piston 8, together with piston rod 9, downward.

With the onset of said movement, the hydraulic fluid is displaced out of the cylinder chamber 3 again in the described manner. At the same time, however, the hydraulic fluid is also conveyed into the lower cylinder chamber part 3a from the additional receiving chamber 33. The hydraulic fluid flows downward via the aperture 35, which is clearly shown in particular in FIG. 9 and of which two are provided so as to be situated mutually oppositely, and via the longitudinal groove 36, which is not shown here but can also be seen from FIG. 9, into the lower cylinder chamber part 3a.

While specific embodiments of the invention have been shown and described in detail to illustrate the inventive principles, it will be understood that the invention may be embodied otherwise without departing from such principles.

The invention claimed is:

1. A hydraulic damping cylinder for a prosthetic knee joint,
  comprising:
  a housing;
  a cylinder chamber provided in the housing and filled with a hydraulic fluid; and
  a piston arranged in the cylinder chamber and movable in the cylinder chamber by way of a piston rod introduced into the cylinder chamber;
  wherein the housing defines at least two receiving chambers separate from and of different size from one another and connected to the cylinder chamber by fluid ducts;
  wherein a throttle device forms a flow resistance for the hydraulic fluid flowing into one of the at least two receiving chambers, and the hydraulic fluid is distributed to the at least two receiving chambers depending on piston movement speed;
  wherein each of the at least two receiving chambers is assigned a separate compression chamber which is filled with a compressible fluid;
  wherein each one of the at least two receiving chambers and respective separate compression chambers are separated from one another by way of a flexible diaphragm.

2. The hydraulic damping cylinder of claim 1, wherein the cylinder chamber is formed by an insert component arranged in the housing.

3. The hydraulic damping cylinder of claim 1, wherein a flow cross-section of the throttle device is adjustable.

4. The hydraulic damping cylinder of claim 1, wherein the throttle device comprises an adjustable throttle element.

5. The hydraulic damping cylinder of claim 1, wherein the flexible diaphragm is arranged to deform if pressure builds up in the corresponding one of the at least two receiving chambers.

6. The hydraulic damping cylinder of claim 1, wherein the at least two receiving chambers are of different size, and hold different amounts of the hydraulic fluid.

7. The hydraulic damping cylinder of claim 6, wherein the at least two receiving chambers comprise a first chamber larger than a second chamber.

8. The hydraulic damping cylinder of claim 7, wherein the throttle device is connected upstream of the first chamber and forms a flow resistance for the hydraulic fluid flowing into the first chamber.

9. A hydraulic damping cylinder comprising:
  a housing;
  a cylinder chamber provided in the housing and filled with a hydraulic fluid; and a piston arranged in the cylinder chamber and movable in the cylinder chamber by way of a piston rod introduced into the cylinder chamber;

wherein the housing defines first and second receiving chambers, the first receiving chamber being larger than the second receiving chamber, the first and second receiving chambers are connected to the cylinder chamber by fluid ducts, and are each separated by a diaphragm from first and second compression chambers, respectively, filled with compressible fluid.

10. The hydraulic damping cylinder of claim 9, further comprising a throttle device located upstream of the first receiving chamber, the throttle device forming a flow resistance for the hydraulic fluid flowing into the first receiving chamber, so that the hydraulic fluid is distributed to the first and second receiving chambers in a manner dependent on a speed of movement of the piston.

11. The hydraulic damping cylinder of claim 10, wherein a flow cross-section of the throttle device is adjustable.

12. The hydraulic damping cylinder of claim 11, wherein the throttle device comprises an adjustable throttle element by means of which a cross-section of a flow bore which leads to the first receiving chamber can be varied.

13. The hydraulic damping cylinder of claim 12, wherein the throttle device is provided in a region of a base of the cylinder chamber, wherein the first receiving chamber is provided in a region of the base of the cylinder chamber, so as to surround the latter at least in sections, whereas the second receiving chamber is provided thereabove, in a region of a cylinder cover element.

14. The hydraulic damping cylinder of claim 10, wherein, upstream of the first and second receiving chambers, there is connected a switching valve by means of which, in a manner dependent on a position of the piston or of the piston rod, flow of the hydraulic fluid can be supplied to a relatively large receiving chamber bypassing the throttle device or via the throttle device.

15. The hydraulic damping cylinder of claim 9, wherein the cylinder chamber is formed by an insert component arranged in the housing.

16. The hydraulic damping cylinder of claim 9, wherein a reversibly closable fluid supply opening is provided via which the compressible fluid can be filled into or drained from the first and second compression chambers.

17. The hydraulic damping cylinder of claim 16, wherein the first and second compression chambers are connected to one another by way of a check valve which opens in a presence of a positive pressure in the compression chamber assigned to a first receiving chamber.

18. The hydraulic damping cylinder of claim 9, wherein the diaphragm is formed from rubber or plastic.

* * * * *